(12) United States Patent
Sirch et al.

(10) Patent No.: US 8,884,076 B2
(45) Date of Patent: *Nov. 11, 2014

(54) METHOD FOR PREPARING POLYMETHYLOLS

(75) Inventors: Tilman Sirch, Schifferstadt (DE); Michael Steiniger, Neustadt (DE); Steffen Maas, Bubenheim (DE); Stefan Rittinger, Mannheim (DE); Stephan Schlitter, Shanghai (CN)

(73) Assignee: BASF SE, Ludwigshafen (DE)

( * ) Notice: Subject to any disclaimer, the term of this patent is extended or adjusted under 35 U.S.C. 154(b) by 336 days.

This patent is subject to a terminal disclaimer.

(21) Appl. No.: 13/133,861

(22) PCT Filed: Dec. 7, 2009

(86) PCT No.: PCT/EP2009/066522

§ 371 (c)(1),
(2), (4) Date: Jun. 9, 2011

(87) PCT Pub. No.: WO2010/066674

PCT Pub. Date: Jun. 17, 2010

(65) Prior Publication Data

US 2012/0004472 A1  Jan. 5, 2012

(30) Foreign Application Priority Data

Dec. 9, 2008  (EP) .................................... 08171040

(51) Int. Cl.
| C07C 27/04 | (2006.01) |
| C08G 63/16 | (2006.01) |
| C08G 18/56 | (2006.01) |
| C07C 29/80 | (2006.01) |
| C07C 29/141 | (2006.01) |
| C08L 67/00 | (2006.01) |
| C08L 75/04 | (2006.01) |

(52) U.S. Cl.
CPC .............. *C07C 29/141* (2013.01); *C08G 63/16* (2013.01); *C08G 18/56* (2013.01); *C08L 67/00* (2013.01); *C07C 29/80* (2013.01); *C08L 75/04* (2013.01)
USPC ............ 568/864; 568/853; 568/854; 568/857

(58) Field of Classification Search
None
See application file for complete search history.

(56) References Cited

U.S. PATENT DOCUMENTS

| 3,808,280 A | 4/1974 | Merger et al. |
| 4,122,290 A | 10/1978 | Immel et al. |
| 4,247,485 A | 1/1981 | Immel et al. |
| 4,288,640 A | 9/1981 | Schuster et al. |
| 4,386,018 A | 5/1983 | Merger et al. |
| 4,386,219 A | 5/1983 | Merger et al. |
| 5,397,439 A | 3/1995 | Kandori et al. |
| 5,532,417 A | 7/1996 | Salek et al. |
| 6,018,074 A | 1/2000 | Kratz et al. |
| 6,187,971 B1 | 2/2001 | Kratz et al. |
| 6,201,160 B1 | 3/2001 | Brudermuller et al. |
| 6,692,616 B2 | 2/2004 | Dernbach et al. |
| 7,112,707 B2 * | 9/2006 | Sirch et al. ..................... 568/854 |
| 7,462,747 B2 | 12/2008 | Sirch et al. |
| 7,767,865 B2 | 8/2010 | Sirch et al. |
| 2002/0189926 A1 | 12/2002 | Dernbach et al. |
| 2003/0088131 A1 | 5/2003 | Dernbach et al. |
| 2007/0015940 A1* | 1/2007 | Pennemann et al. .......... 564/420 |
| 2008/0167506 A1 | 7/2008 | Sirch et al. |
| 2010/0101931 A1 | 4/2010 | Pinkos et al. |
| 2010/0113805 A1 | 5/2010 | Windecker et al. |
| 2010/0113836 A1 | 5/2010 | Sirch et al. |
| 2010/0168445 A1 | 7/2010 | Pinkos et al. |
| 2010/0240913 A1 | 9/2010 | Pinkos et al. |
| 2010/0256398 A1 | 10/2010 | Pinkos et al. |
| 2011/0015429 A1 | 1/2011 | Pinkos et al. |
| 2011/0130318 A1 | 6/2011 | Maas et al. |

FOREIGN PATENT DOCUMENTS

| DE | 1941633 A1 | 3/1971 |
| DE | 1957591 A1 | 5/1971 |
| DE | 2040501 A1 | 2/1972 |
| DE | 27 02 582 A1 | 7/1978 |
| DE | 28 13 201 A1 | 10/1979 |
| EP | 44444 A1 | 1/1982 |
| GB | 1362071 A | 7/1974 |
| JP | H05201898 A | 8/1993 |
| JP | H06172235 A | 6/1994 |

(Continued)

OTHER PUBLICATIONS

International Preliminary Report on Patentability for PCT/EP2009/066522 dated Jun. 14, 2011.
International Search Report for PCT/EP2009/066522 dated Nov. 4, 2010.

*Primary Examiner* — Sudhakar Katakam
(74) *Attorney, Agent, or Firm* — Drinker Biddle & Reath LLP

(57) ABSTRACT

The present invention relates to a process for distilling an aqueous polymethylol mixture which comprises a polymethylol of the formula (I)

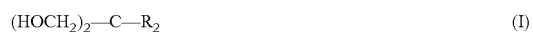

$$(HOCH_2)_2-C-R_2 \qquad (I)$$

in which each R is independently a further methylol group or an alkyl group having 1 to 22 carbon atoms or an aryl or aralkyl group having 6 to 22 carbon atoms, a tertiary amine, water and the adduct of tertiary amine and formic acid (amine formate), which comprises performing the distillation in a distillation column which is connected at the bottom to an evaporator, the bottom temperature being above the evaporation temperature of the monoester of formic acid and polymethylol (polymethylol formate) which forms during distillation. The present invention further relates to a composition comprising polymethylol and 1 to 10 000 ppm by weight of polymethylol formate, and to the use thereof.

14 Claims, No Drawings

(56) References Cited

FOREIGN PATENT DOCUMENTS

| JP | H0987273 A | 3/1997 |
| JP | 2003525218 A | 8/2003 |
| JP | 2010518174 A | 5/2010 |
| WO | WO-9532171 A1 | 11/1995 |
| WO | WO-97/17313 A1 | 5/1997 |
| WO | WO-98/28253 A1 | 7/1998 |
| WO | WO-01/47847 A1 | 7/2001 |
| WO | WO-01/47848 A1 | 7/2001 |
| WO | WO-01/47849 A1 | 7/2001 |
| WO | WO-2008107333 A1 | 9/2008 |
| WO | WO-2010031719 A1 | 3/2010 |
| WO | WO-2010066673 A2 | 6/2010 |
| WO | WO-2010066674 A2 | 6/2010 |
| WO | WO-2010/079187 A1 | 7/2010 |

* cited by examiner

METHOD FOR PREPARING POLYMETHYLOLS

CROSS-REFERENCE TO RELATED APPLICATIONS

This application is a national stage application (under 35 U.S.C. §371) of PCT/EP2009/066522, filed Dec. 7, 2009, which claims benefit of European application 08171040.2, filed Dec. 9, 2008.

BACKGROUND OF THE INVENTION

The invention relates to a process for distilling an aqueous polymethylol mixture which is obtained in the preparation of polymethylols from alkanals and formaldehyde. The present invention further relates to a composition comprising polymethylol and 1 to 000 ppm by weight of polymethylol formate, and to the use thereof.

Polymethylols, for example neopentyl glycol ("NPG") and trimethylolpropane ("TMP"), are used in the plastics sector for production of paint systems, coatings, polyurethanes and polyesters.

On the industrial scale, polymethylols are usually prepared by the Cannizzaro process. In order to prepare trimethylolpropane by this process, n-butyraldehyde is reacted with an excess of formaldehyde in the presence of an inorganic base. This likewise forms one equivalent of an inorganic formate as a coproduct. The separation of the salt of trimethylolpropane is complicated and requires additional work. Moreover, the inorganic salt—if it can be utilized in a profitable manner—must be worked up and purified. The occurrence of the coproduct otherwise constitutes a loss of the stoichiometrically used amounts of sodium hydroxide solution and formaldehyde. In addition, the yields in this inorganic Cannizzaro reaction are unsatisfactory in relation to n-butyraldehyde, since high-boiling constituents are formed in the course of the reaction, which cannot be utilized further.

Similar problems to those outlined for trimethylolpropane exist in the preparation of other polymethylols such as trimethylolethane (from n-propanal and formaldehyde) or trimethylolbutane (from n-pentanal and formaldehyde) or neopentyl glycol (from isobutyraldehyde and formaldehyde).

To avoid these disadvantages, WO 98/28253 disclosed a multistage process for preparing polymethylols, in which aldehydes having 2 to 24 carbon atoms are first condensed in a first stage (aldol reaction) with formaldehyde using tertiary amines as a catalyst to give the corresponding methylolalkanals, and then hydrogenated in a further stage (hydrogenation) to give the corresponding polymethylols. This multistage process is typically referred to as the hydrogenation process. This process is low in coproducts.

After the first stage of the hydrogenation process, unconverted aldehydes and a portion of the amine base are generally removed by distillation from the methylolalkanals formed and recycled.

In the distillation bottoms there remain—as well as the methylolalkanals formed—water, the adducts of formic acid and the tertiary amines used (amine formate) and formic acid itself.

In general, the polymethylolalkanal is obtained by these processes as a 20 to 70% by weight aqueous solution.

The aqueous polymethylolalkanal-containing solution is hydrogenated in a second stage in order to convert the polymethylolalkanals to the corresponding polymethylols, such as TMP or NPG.

In the course of hydrogenation, side reactions are generally observed, such as a redissociation of the methylolalkanal to free alkanal and formaldehyde and additionally ether, ester and acetal formation.

These side reactions lead to a low hydrogenation selectivity and to low yields of polymethylols.

These by-products can also impair the quality of the polymethylols formed and the use thereof in particular applications. For instance, formates present in the end product can decompose to form formic acid. Formic acid can, for example, catalyze the hydrolysis of urethane or ester bonds, which leads to accelerated aging of coatings and polymers.

In the context of the present invention, it has now been found that especially monoesters of formic acid and of the polymethylols formed (polymethylol formate) contribute to the formate content in the end product.

It was therefore an object of the present invention to provide a process for purifying an aqueous polymethylol mixture in order to obtain, polymethylols with a low content of polymethylol formates.

The object of the present invention is achieved by a process for distilling an aqueous polymethylol mixture which comprises a polymethylol of the formula (I)

in which each R is independently a further methylol group or an alkyl group having 1 to 22 carbon atoms or an aryl or aralkyl group having 6 to 22 carbon atoms, a tertiary amine, water and the adduct of tertiary amine and formic acid (amine formate), which comprises performing the distillation of the hydrogenation discharge in a distillation column which is connected at the bottom to an evaporator, the bottom temperature being above the evaporation temperature of the monoester of formic acid and polymethylol (polymethylol formate) which forms during the distillation.

DETAILED DESCRIPTION OF THE INVENTION

The aqueous polymethylol mixture used in the process preferably has the following composition:
20 to 90% by weight of polymethylol (I),
0 to 5% by weight of methanol,
0 to 5% by weight of tertiary amine,
0 to 5% by weight of organic secondary compounds,
0.01 to 5% by weight of the adduct of tertiary amine and formic acid (amine formate), remainder water.

The aqueous polymethylol mixture more preferably has the following composition:
50 to 80% by weight of polymethylol (I),
0.1 to 3% by weight of methanol,
0.01 to 5% by weight of tertiary amine,
0 to 5% by weight of organic secondary compounds,
0.01 to 5% by weight of the adduct of tertiary amine and formic acid (amine formate), remainder water.

Such aqueous polymethylol mixtures are preferably obtained by multistage reaction of alkanals with formaldehyde. The aqueous polymethylol mixture is preferably obtained by the hydrogenation process.

However, it is also possible to perform the process according to the invention for distilling an aqueous polymethylol mixture with a polymethylol mixture which has been obtained by organic Cannizzaro reaction (strong organic base and formaldehyde).

As mentioned above, the aqueous polymethylol mixture is preferably obtained in a multistage hydrogenation process involving, in stage a), condensing alkanals in an aldol reaction with formaldehyde in the presence of tertiary amines as a catalyst to give methylolalkanals of the formula (II) where each R is independently as defined above

and then, in stage b), distillatively separating the reaction mixture obtained from stage a) into bottoms comprising predominantly compounds of the formula (II), and a top stream comprising low boilers, and, in stage c), hydrogenating the bottoms discharge from stage b).

In the first process stage a) (aldol reaction), alkanals are generally reacted in an aldol reaction with formaldehyde in the presence of tertiary amines as a catalyst.

Formaldehyde is generally used in the process as an aqueous formaldehyde solution. Industrially available formaldehyde is typically sold in aqueous solution in concentrations of 30, 37 and 49% by weight. However, it is also possible to use formaldehyde solutions of up to 60% by weight in the process.

Industrial formaldehyde generally comprises formic acid as a result of the preparation. The degradation products of formic acid can reduce the service life of the hydrogenation catalyst in the downstream hydrogenation stage, which can result in a decrease in the yield of polymethylols. In a particular embodiment, formaldehyde which has a formic acid content of 150 ppm or less is used. Such formaldehyde can, as described in application PCT/EP2008/052240, be obtained by treating formaldehyde or an aqueous formaldehyde solution with basic ion exchangers. Useful anion exchangers include strongly basic, weakly basic or moderately basic, gel-form or macroporous ion exchangers known per se. These are, for example, anion exchangers of the polystyrene, resin structure crosslinked with divinylbenzene, with tertiary amino groups as functional groups. Also useful are ion exchangers based on acrylic acid or methacrylic acid crosslinked with divinylbenzene, or resins produced by condensation of formaldehyde and phenol. Specific examples include the commercial products Ambersep® 900, Amberlyst® and Amberlite® from Rohm and Haas, Philadelphia, USA and Lewatit® from Lanxess, Leverkusen.

In the process according to the invention, it is possible to use alkanals with a methylene group in the α position to the carbonyl group.

It is possible with preference to use aliphatic alkanals having 2 to 24 carbon atoms as starting materials, which may be straight-chain or branched or else comprise alicyclic groups.

It is equally possible to use araliphatic alkanals as starting materials, provided that they comprise a methylene group in the α position to the carbonyl group. In general, aralkylalkanals having 8 to 24 carbon atoms and preferably having 8 to 12 carbon atoms are used as starting materials, for example phenylacetaldehyde. Preference is given to aliphatic alkanals having 2 to 12 carbon atoms, for example 3-ethyl-, 3-n-propyl-, 3-isopropyl-, 3-n-butyl-, 3-isobutyl-, 3-sec-butyl-, 3-tert-butylbutanal and corresponding -n-pentanals, -n-hexanals, -n-heptanals; 4-ethyl-, 4-n-propyl-, 4-isopropyl-, 4-n-butyl-, 4-isobutyl-, 4-sec-butyl-, 4-tert-butylpentanals, -n-hexanals, -n-heptanals; 5-ethyl-, 5-n-propyl-, 5-isopropyl-, 5-n-butyl-, 5-isobutyl-, 5-sec-butyl-, 5-tert-butyl-n-hexanals, -n-heptanals; 3-methylhexanal, 3-methylheptanal; 4-methylpentanal, 4-methylheptanal, 5-methylhexanal, 5-methylheptanal; 3,3,5-trimethyl-n-pentyl-, 3,3-diethylpentyl-, 4,4-diethylpentyl-, 3,3-dimethyl-n-butyl-, 3,3-dimethyl-n-pentyl-, 5,5-dimethylheptyl-, 3,3-dimethylheptyl-, 3,3,4-trimethylpentyl, 3,4-dimethylheptyl-, 3,5-dimethylheptyl-, 4,4-dimethylheptyl-, 3,3-diethylhexyl-, 4,4-dimethylhexyl-, 4,5-dimethylhexyl-, 3,4-dimethylhexyl-, 3,5-dimethylhexyl-, 3,3-dimethylhexyl-, 3,4-diethylhexyl-, 3-methyl-4-ethylpentyl, 3-methyl-4-ethylhexyl-, 3,3,4-trimethylpentyl-, 3,4,4-trimethylpentyl-, 3,3,4-trimethylhexyl-, 3,4,4-trimethylhexyl-, 3,3,4,4-tetramethylpentylaldehyde; especially $C_2$- to $C_{12}$-n-alkanals.

In addition to the preferred use of isobutyraldehyde, which is used to prepare neopentyl glycol, it is also possible with preference to use, as starting materials, n-butyraldehyde to prepare trimethylolpropane, acetaldehyde to prepare pentaerythritol, propionaldehyde to prepare trimethylolethane, and n-pentanal to prepare trimethylolbutane.

The tertiary amines used may be amines as described, for example, in DE-A 28 13 201 and DE-A 27 02 582. Particular preference is given to tri-n-alkylamines, especially triethylamine, tri-n-propylamine, tri-n-butylamine and trimethylamine.

Very particular preference is given to trimethylamine ("TMA"), triethylamine ("TEA") and tri-n-propylamine ("TPA"), since these compounds generally have a lower boiling point than the polymethylols formed with preference, and the distillative removal from the reaction mixture is therefore facilitated. Particular preference is given to using trimethylamine ("TMA") as the tertiary amine in the reaction.

The aldol reaction can be performed with or without addition of organic solvents or solubilizers. The addition of solvents or solubilizers may be found to be advantageous especially in the case of use of long-chain alkanals as starting materials. The use of solvents which form suitable low-boiling azeotropic mixtures with the low-boiling compounds in the individual distillations of the process according to the invention may allow the energy expenditure in these distillations to be lowered and/or the distillative removal of the low boilers from the high-boiling compounds to be facilitated.

Examples of suitable solvents include cyclic and acyclic ethers such as THF, dioxane, methyl tert-butyl ether, or alcohols such as methanol, ethanol or 2-ethylhexanol.

In the aldol reaction, the molar ratio of alkanal added fresh in each case to the amount of formaldehyde added is appropriately between 1:1 and 1:5, preferably 1:2 to 1:3.5.

The amount of tertiary amine catalyst added in the aldol reaction in relation to the alkanal added is generally 0.001 to 0.2 and preferably 0.01 to 0.07 equivalent, i.e. the amine is typically used in catalytic amounts.

The aldol reaction is generally performed at a temperature of 5 to 100° C. and preferably of 15 to 80° C., and the residence time is generally set to 0.25 to 12 hours depending on the temperature.

The reaction regimes described for the aldol reaction can be performed at a pressure of generally 1 to 30 bar, preferably 1 to 15 bar, more preferably 1 to 5 bar, and appropriately under the autogenous pressure of the reaction system in question.

The aldol reaction can be performed batchwise or continuously. The aldol reaction is preferably performed in a continuous stirred tank reactor or a continuous stirred tank cascade. To establish the residence time, a portion of the reaction discharge from one stirred tank can be recycled into the particular stirred tank reactor.

The discharge from the aldol reaction typically comprises unconverted starting compounds, such as formaldehyde, alkanals and the tertiary amine catalyst used, with or without water.

The discharge from the aldol reaction further comprises a methylolalkanal of the formula (II)

in which each R is independently a further methylol group or an alkyl group having 1 to 22 carbon atoms or an aryl or aralkyl group having 6 to 22 carbon atoms. Examples of methylolalkanals are hydroxypivalaldehyde, which is formed in the case of use of isobutyraldehyde as a reactant, or dimethylolbutanal, which is formed in the case of use of n-butyraldehyde as a reactant.

Typically, the discharge also comprises impurities and by-products from the aldol reaction, such as formic acid, which can form by Canizzaro or Tishchenko reaction from formaldehyde, and formate salts of the amine catalysts used, such as trimethylammonium formate.

The discharge from the aldol reaction is subsequently typically worked up by distillation (stage b)).

In this case, the discharge from the aldol reaction is sent to a distillation apparatus, typically a column, in which it is separated into volatile and nonvolatile constituents. The distillation conditions are generally selected such that one fraction forms from low boilers, in which the essential components present are unconverted alkanal and formaldehyde, with or without water, formaldehyde and methanol. This so-called low boiler fraction can be recycled into the first stage of the hydrogenation process, the aldol reaction, or be sent to a further workup stage.

After removal of the low boiler fraction, what remains in the distillative workup outlined is a nonvolatile bottom product which consists essentially of methylolalkanal (II), for example hydroxypivalaldehyde, water, formic acid and amine formate.

In the case of use of TMA as the tertiary amine, the distillation conditions are selected such that TMA is also present partly in the low boiler fraction and is present to a minor degree in the bottom product. In the case of use of amines having a higher boiling point than TMA, the distillation conditions are selected such that the tertiary amines are enriched in the bottom product.

The distillative removal should preferably be effected at moderate pressure in order not to decompose the methylolalkanals (II) by elevated temperature. For example, hydroxypivalaldehyde can be converted to hydroxypivalic acid neopentyl glycol ester (HPN). On the other hand, the pressure should not be too low, in order still to condense the low-boiling alkanals, such as isobutyraldehyde, and amine base, for example trialkylamine, such as trimethylamine, at the top.

The distillation should also not take place at too low a pressure because the solubility of alkanal (II), such as hydroxypivalaldehyde (HPA), in the aqueous solution abruptly declines to about 1 to 3% by weight generally below about 60° C., depending on the alkanal and methanol content.

In addition, the discharge from the aldol reaction should be separated such that the amount of methanol in the low boiler stream is kept as low as possible, in order that the methanol concentration does not accumulate in the aldol reaction. Methanol is generally introduced via the aqueous formaldehyde solution, which, according to the preparation conditions, comprises about 1 to 3% by weight of methanol.

The boiling point of methanol is generally lower than that of the unconverted alkanal, such that methanol is enriched at the top of the column, thus resulting in an accumulation of the methanol concentration in the process.

In order to keep the methanol concentration low, various measures can be taken.

One advantageous measure is to use low-methanol formaldehyde as a reactant in the aldol reaction.

It is further possible to discharge methanol from the process together with unconverted alkanal, which leads to a loss of alkanal.

In a preferred embodiment, the distillation is, however, performed under specific conditions, such that methanol is retained sufficiently in the column bottoms. This preferred embodiment of the distillative separation of the discharge from the aldol reaction is described in application PCT/EP2008/052240.

In this embodiment, the distillative separation into a low boiler fraction and the bottom product is performed generally at 50 to 200° C., preferably at 90 to 160° C., and at a pressure of generally 0.1 mbar to 10 bar, preferably of 0.5 to 5 bar, especially at atmospheric pressure, in a distillation column. The distillation column is typically operated at a top pressure in the range from 0.5 to 1.5 bar.

In the top region, a two-stage condensation is preferably provided, in which the vapors are first conducted into a partial condenser operated at a temperature in the range from 50 to 80° C., the condensate of which is at least partly recycled into the distillation column, and in which the vapors uncondensed in the partial condenser are fed to a downstream condenser operated at a temperature in the range from −40 to +30° C., the condensate of which is at least partly discharged.

The condensate of the partial condenser is preferably recycled into the distillation column to an extent of more than 70% by weight and more preferably fully. The condensate is preferably recycled into the top of the column. The condensate of the downstream condenser is preferably discharged to an extent of at least 70% by weight, and is especially discharged completely.

The partial condenser is operated at a temperature in the range from 50 to 80° C. and preferably 55 to 60° C. The downstream condenser is operated at a temperature in the range from −40 to +30° C. and preferably −10 to +10° C. The top pressure is more preferably 1 to 1.2 bar.

The bottom of the distillation column is preferably connected to an evaporator with a short residence time, which is operated at a temperature in the range from 90 to 130° C., more preferably from 100 to 105° C. The evaporator is more preferably a falling film evaporator; it is also possible with preference to use a wiped film evaporator or a short path evaporator. What is essential is that a short residence time and hence a low thermal stress are achieved. The evaporator can be supplied with heat in a suitable manner, for example with 4 bar steam.

The distillation column preferably has internals for increasing the separating performance. The reaction discharge of the aldolization is preferably fed in within a spatial region between ¼ and ¾ of the theoretical plates of the distillation column, more preferably in a spatial region between ⅓ and ⅔ of the theoretical plates of the distillation column. For example, the feed may be somewhat above the middle of the theoretical plates (ratio 3:4).

The distillative internals may, for example, be present as a structured packing, for example as a sheet metal packing such as Mellapak 250 Y or Montz Pak, B1-250 type. It is also possible for a structured packing with relatively low or increased specific surface area to be present, or a fabric packing or a structured packing with another geometry such as Mellapak 252 Y can be used. What are advantageous in the case of use of these distillative internals are the low pressure drop and the low specific liquid holdup compared to, for example, valve trays.

The condensate obtained in the partial condenser is predominantly water, which is preferably fed to the column completely as reflux. In the case of preparation of NPG, for example, the condensate obtained may be a mixture which comprises about 10% by weight of isobutyraldehyde, about 5% by weight of amine base such as trimethylamine, about 1% by weight of hydroxypivalaldehyde and about 5% by weight of methanol as well as water, when isobutyraldehyde is used as the reactant. In these cases, the residual vapors comprise the predominant amount of isobutyraldehyde and amine base such as trimethylamine. These are precipitated very substantially in the downstream condenser. The cooling medium used here may preferably be very cold water (e.g. about 5° C.) or a coolant mixture (e.g. glycol-water at, for example, −20° C.). Preference is given to discharging a mixture enriched with methylolalkanal (II), for example hydroxypivalaldehyde or dimethylolbutanal, from the bottom of the evaporator. Discharge from the circulation system is also possible.

The relatively nonvolatile bottom product from the distillative separation of the discharge from the aldol reaction can, to reduce the thermal stress, be cooled before further workup in a cooler with a cooler temperature in the range from 50 to 80° C., more preferably 55 to 60° C.

The bottom discharge thus obtained from stage b) can subsequently be hydrogenated in stage c).

The bottom discharge from stage b) of the hydrogenation process comprises methylolalkanal of the general formula (II) and is hydrogenated in stage c) of the hydrogenation process to the corresponding polymethylols ("hydrogenation").

In the hydrogenation, preference is given to using catalysts which comprise at least one metal of transition groups 8 to 12 of the Periodic Table of the Elements, such as Fe, Ru, Os, Co, Rh, Ir, Ni, Pd, Pt, Cu, Ag, An, Zn, Cd, Hg, preferably Fe, Co, Ni, Cu, Ru, Pd, Pt, more preferably Cu, preferably on a support material.

The support material used is preferably a support material composed of the oxides of titanium, of zirconium, of hafnium, of silicon and/or of aluminum.

The usable catalysts can be prepared by processes known from the prior art for preparing such supported catalysts. Preference may also be given to using supported catalysts which comprise copper on an aluminum oxide- or titanium oxide-containing support material in the presence or absence of one or more of the elements magnesium, barium, zinc or chromium. Such catalysts and preparation thereof are known from WO 99/44974.

In addition, supported copper catalysts as described, for example, in WO 95/32171 and the catalysts disclosed in EP-A 44 444 and DE 19 57 591 are suitable for the hydrogenation.

The hydrogenation can be performed batchwise or continuously, for example in a reactor tube filled with a catalyst bed, in which the reaction solution is passed over the catalyst bed, for example in trickle or liquid phase mode, as described in DE-A 19 41 633 or DE-A 20 40 501. It may be advantageous to recycle a substream of the reaction discharge, if appropriate with cooling, and to pass it through the fixed catalyst bed again. It may equally be advantageous to perform the hydrogenation in a plurality of reactors connected in series, for example in 2 to 4 reactors, in which case the hydrogenation reaction in the individual reactors upstream of the last reactor is performed only up to a partial conversion of, for example, 50 to 98%, and only in the last reactor is the hydrogenation completed. It may be appropriate to cool the hydrogenation discharge from the preceding reactor before its entry into the next reactor, for example by means of cooling apparatus or by injecting cold gases, such as hydrogen or nitrogen, or introducing a substream of cold reaction solution.

The hydrogenation temperature is generally between 50 and 180° C., preferably 90 and 140° C. The hydrogenation pressure employed is generally 10 to 250 bar, preferably 20 to 120 bar.

The hydrogenation feed is generally mixed with tertiary amine upstream of the hydrogenation reactor inlet until the hydrogenation discharge has a pH of 7 to 9. It is also possible to feed the hydrogenation feed and the tertiary amine separately into the reactor and to mix them there. The tertiary amines used may be the aforementioned tertiary amines, especially TMA.

The reaction discharge from the hydrogenation (stage c)) is an aqueous polymethylol mixture which comprises a polymethylol of the formula (I)

in which each R is independently a further methylol group or an alkyl group having 1 to 22 carbon atoms or an aryl or aralkyl group having 6 to 22 carbon atoms, a tertiary amine, water and the adduct of tertiary amine and formic acid (amine formate).

As mentioned above, the aqueous polymethylol mixture preferably has the following composition:
20 to 90% by weight of polymethylol (I),
0 to 5% by weight of methanol,
0 to 5% by weight of tertiary amine,
0 to 5% by weight of organic secondary compounds,
0.01 to 5% by weight of the adduct of tertiary amine and formic acid (amine formate), remainder water.

The aqueous polymethylol mixture more preferably has the following composition:
50 to 80% by weight of polymethylol (I),
0.1 to 3% by weight of methanol,
0.01 to 5% by weight of tertiary amine,
0 to 5% by weight of organic secondary compounds,
0.01 to 5% by weight of the adduct of tertiary amine and formic acid (amine formate), remainder water.

The organic secondary compound present may, for example, be the hydrogenated form of the alkanal used, specifically an alcohol of the formula (III)

in which each R is independently as defined above.

The aqueous polymethylol mixture is purified in accordance with the invention by removing low boilers from the polymethylol compound.

According to the invention, the low boilers are removed from the aqueous polymethylol mixture by distillation.

The distillation is preferably performed in such a way that low boilers, such as water, alcohol of the formula (III), methanol and tertiary amine, are removed under reduced pressure via the top, especially when the amine used has a lower boiling point than the polymethylol formed, as is the case for TMA, TEA and TPA.

When a tertiary amine which has a higher boiling point than the polymethylol formed is used, the tertiary amine is removed at the bottom together with the polymethylol formed and enriched in the column bottom in a downstream distillation stage, while polymethylol is drawn off as the top product.

In the context of the present invention, it has been found that a portion of the amine formates reacts during the distillation in the column bottom or in the stripping section of the column with polymethylol compounds to form the free amines and the formates of the polymethylol compounds. This preferably forms the monoester of formic acid and of the polymethylol compound, which is referred to in the context of this disclosure as polymethylol formate.

The amines released by the transesterification reaction are generally removed in the distillation together with the other low boilers at the top of the column.

The distillation should therefore be regulated such that the concentration of the polymethylol formates formed in the bottom discharge is kept low and the target product, the polymethylol, is of maximum purity. According to the invention, this is done by selecting, in the distillation, a bottom temperature above the evaporation temperature of the polymethylol formate, such that the polymethylol formates are completely or very substantially completely converted to the gas phase by evaporation. The improvement in the yield and in the product quality brought about by the inventive measure is probably attributable to the fact that the polymethyol formates typically have higher boiling points than the other low boilers, and the polymethylol formates are therefore generally precipitated in the rectifying section of the columns at an appropriate reflux ratio. The polymethylol formates precipitated in the rectifying section can hydrolyze with water to reform formic acid and the polymethylol compound. The formic acid is typically removed at the top of the column, while the polymethylol compound can generally be discharged from the column bottom.

In a preferred embodiment, the distillation is preferably carried out as follows:

In this preferred embodiment, the condenser is generally operated at a temperature at which the predominant portion of the low boilers is condensed at the corresponding top pressure.

In general, the operating temperature of the condenser is in the range from 0 to 80° C., preferably 20 to 50° C.

The cooling medium used here may preferably be very cold water (e.g. about 5° C.) or a coolant mixture (e.g. glycol-water at, for example, −20° C.).

The top pressure is more preferably 0.001 to 0.9 bar, more preferably 0.01 to 0.5 bar. On the industrial scale, the vacuum is typically obtained by means of a steam ejector. In the column bottom, preference is given to establishing a temperature which is above the evaporation temperature of the polymethylol formate, such that the polymethylol formate is converted completely or very substantially completely to the gas phase. Particular preference is given to establishing a temperature which is 5% to 50% above the boiling temperature of the polymethylol formate and most preferably 10% to 20% above the boiling temperature of the polymethylol formate.

For example, in the case of preparation of NPG using TMA as the tertiary amine and a pressure at the top of the column of 175 mbar, a column bottom temperature of preferably 150 to 170° C., more preferably of 160 to 165° C., can be established.

The reflux at the top of the column is generally adjusted such that the predominant amount of the polymethylol formate is retained in the column.

The condensate obtained at the condenser is preferably recycled into the distillation column to an extent of more than 30% by weight, preferably to an extent of more than 60% by weight. The condensate is preferably recycled into the top of the column. The energy required for the evaporation is typically introduced by means of an evaporator in the column bottom.

The evaporator is typically a natural circulation evaporator or forced circulation evaporator. However, it is also possible to use evaporators with a short residence time, falling film evaporators, helical tube evaporators, wiped film evaporators or a short path evaporator. The evaporator can be supplied with heat in a suitable manner, for example with 16 bar steam or heat carrier oil.

The distillation column preferably has internals for increasing the separating performance. The distillative internals may, for example, be present as a structured packing, for example as a sheet metal packing such as Mellapak 250Y or Montz Pak, B1-250 type. It is also possible for a structured packing with relatively low or increased specific surface area to be present, or it is possible to use a fabric packing or a structured packing with another geometry, such as Mellapak 252Y. What are advantageous in the case of use of these distillative internals are the low pressure drop and the low specific liquid holdup compared to, for example, valve trays. The internals may be present in one or more sections.

The discharge from the hydrogenation is preferably fed in within a spatial region between ¼ and ¾ of the theoretical plates of the distillation column, more preferably in a spatial region between ⅓ and ⅔ of the theoretical plates of the distillation column. For example, the feed may be somewhat above the middle of the theoretical plates (ratio 3:4).

The number of theoretical plates is generally in the range from 5 to 30, preferably 10 to 20.

The condensate obtained in the condenser is a mixture of low boilers which is fed to the column as described above, predominantly as reflux. For example, the low boiler mixture may comprise amine, water and alcohols of the formula (III), such as isobutanol from isobutyraldehyde or n-butanol from n-butyraldehyde, and methanol from formaldehyde.

The uncondensed residual vapors may, in an energetically advantageous manner, be sent directly in gaseous form to incineration, or are supplied to a distillation column operating close to ambient pressure. This downstream column serves for further distillative separation of the condensate.

Preference is given to discharging, from the bottom of the evaporator, a discharge which comprises predominantly the polymethylol compound. Discharge from the circulation system of the evaporator is also possible.

The bottoms discharge is referred to in the context of the present invention as "crude polymethylol".

The "crude polymethylol" obtained in accordance with the invention comprises a smaller proportion of polymethyol formate compared to the prior art. The proportion of polymethyol formate is preferably less than 1500 ppm by weight, preferably less than 1200 ppm by weight, more preferably less than 800 ppm by weight and especially preferably less than 600 ppm by weight.

The crude polymethylol further comprises polymethylol of the formula (I)

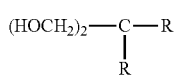
(I)

in which each R is independently a further methylol group or an alkyl group having 1 to 22 carbon atoms or an aryl or aralkyl group having 6 to 22 carbon atoms, and also hydroxy acid of the formula (IV)

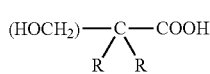
(IV)

in which each R is independently as defined above.

The crude polymethylol preferably has the following composition:
90 to 99% by weight of polymethylol (I),
0.01 to 5% by weight of hydroxy acid of the formula (IV),
0 to 5% by weight of organic secondary compounds.

The crude polymethylol more preferably has the following composition:
95 to 99% by weight of polymethylol (I),
0.1 to 2% by weight of hydroxy acid of the formula (IV),
0 to 3% by weight of organic secondary compounds.

As described above, such a crude polymethylol is preferably obtained by multistage reaction of alkanals with formaldehyde.

The crude polymethylol is preferably obtained by the hydrogenation process.

In order to remove the relatively high-boiling acidic components present in the bottoms, especially hydroxy acids of the formula (IV), with low loss of polymethylol compound, the bottoms evaporator used in the distillation is, in a particularly preferred embodiment, at least one evaporator with short residence time, for example a falling film evaporator with residue discharge, a thin film evaporator or helical tube evaporator.

In a particular embodiment, the bottom of the column may be configured as a tapering bottom, in order to further reduce the residence time in the column bottom.

The distillation of the crude polymethylol is preferably performed under the following conditions:

Advantageously, the condensate obtained in the condenser is recycled into the distillation column (reflux stream) to an extent of more than 30% by weight, more preferably to an extent of more than 50% by weight. The condensate is preferably recycled into the top of the column.

The condenser is operated at a temperature in the range from 50 to 180° C., preferably 130 to 160° C.

The cooling medium used here may preferably as far as possible be water, which at the same time evaporates.

The top pressure is more preferably 0.001 to 0.9 bar.

The vacuum is typically generated on the industrial scale by means of a steam ejector.

The bottom temperature is generally selected such that polymethylol is converted to the gas phase, while hydroxy acid of the formula (IV) remains in the column bottom. Preference is given to establishing a bottom temperature which is 100 to 150%, preferably 105 to 140%, more preferably 110 to 130%, of the boiling temperature of the polymethylol.

For example, in the case of preparation of NPG using TMA as the tertiary amine and a pressure at the top of the column of 150 mbar, preference is given to establishing a column bottom temperature of 150 to 200° C., more preferably of 160 to 190° C.

The bottom of the distillation column is preferably connected to at least one evaporator with short residence time.

The bottom of the distillation column and the evaporator with short residence time together constitute, by definition, the evaporation stage.

According to the disclosure, the residence time of the evaporation stage is calculated by dividing the volume of the liquid holdup in the hot part of the column ($V_{holdup}$) by the sum of reflux and feed volume flow of the column ($V_{holdup}$/(feed stream+reflux stream)), the liquid holdup in the hot part of the column ($V_{holdup}$) being calculated from the volume of the holdup of the column bottom ($V_{holdup,\ bottom}$) plus the volume of the holdup of the evaporator ($V_{holdup,\ evaporator}$) ($V_{holdup}=V_{holdup,\ bottom}+V_{holdup,\ evaporator}$).

The residence time in the evaporation stage is advantageously less than 45 minutes, preferably less than 30 minutes, more preferably less than 15 minutes, especially preferably less than 10 minutes and most preferably less than 5 minutes.

In general, it is preferred to select the residence time in the evaporation stage such that a shorter residence time is correspondingly established at higher bottom temperatures.

At a bottom temperature which is in the range from 130 to 150% of the boiling temperature of the polymethylol, the residence time in the evaporation stage is preferably 5 minutes and less, more preferably 4 minutes and less, and most preferably 3 minutes and less.

At a bottom temperature which is within the range from 120 to 130% of the boiling temperature of the polymethylol, the residence time in the evaporation stage is preferably 30 minutes and less, more preferably 15 minutes and less and most preferably 10 minutes and less, and especially preferably 5 minutes and less.

At a bottom temperature which is within the range from 100 to 120% of the boiling temperature of the polymethylol, the residence time in the evaporation stage is preferably 45 minutes and less, more preferably 30 minutes and less and most preferably 15 minutes and less, and especially preferably 10 minutes and less.

In a further particular embodiment, the evaporator with short residence time is connected to at least one further evaporator with short residence time.

The bottom of the distillation column and the evaporator with short residence time, in this preferred embodiment, by definition, together constitute the first evaporation stage. The further evaporator(s) with short residence time, by definition, form(s) the second or the (1+n)th (where n≥2) evaporation stage.

The evaporator with short residence time is preferably connected to one further evaporator with short residence time (two-stage configuration).

In this embodiment, the predominant portion of the energy needed for evaporation is usually introduced in the first evaporation stage. In the second evaporator stage, the higher temperature required for evaporation can then be achieved with a shorter residence time, such that the residence time in the second evaporation stage is shorter.

The first stage is preferably configured as a falling film evaporator or helical tube evaporator.

The second stage of this particular embodiment is preferably a falling film evaporator, helical tube evaporator or thin layer evaporator.

According to the disclosure, the residence time in the first evaporation stage is calculated by dividing the volume of the liquid holdup in the hot part of the column ($V_{holdup}$) by the sum of reflux and feed volume flow of the column ($V_{holdup}$/(feed stream+reflux stream)), the liquid holdup in the hot part of the column ($V_{holdup}$) being calculated from the volume of the holdup of the column bottom ($V_{holdup,\ bottom}$) plus the volume of the holdup of the evaporator ($V_{holdup,\ evaporator}$) ($V_{holdup}=V_{holdup,\ bottom}+V_{holdup,\ evaporator}$). According to the disclosure, the residence time of the second evaporation stage is calculated by dividing the liquid holdup of the second evaporator by the feed stream of the second evaporator.

According to the disclosure, the residence time of the (1+n)th evaporation stage is accordingly calculated by dividing the liquid holdup of the (1+n)th evaporator by the feed stream of the (1+n)th evaporator.

In this preferred embodiment, the bottom temperature in the first evaporation stage is advantageously above the evaporation temperature of the polymethylol.

The bottom temperature in the first evaporation stage is preferably 100 to 130%, more preferably 110 to 125%, of the boiling temperature of the polymethylol.

The temperature in the second evaporation stage is generally selected such that the polymethylol is converted virtually completely to the gas phase.

The temperature in the second evaporation stage is preferably 105 to 150%, more preferably 120 to 150%, especially preferably 130 to 140%, of the boiling temperature of the polymethylol.

The residence time in the first evaporation stage is advantageously less than 45 minutes, preferably less than 30 minutes, more preferably less than 15 minutes, especially preferably less than 10 minutes and most preferably less than 5 minutes. The residence time in the second evaporation stage is advantageously less than 30 minutes, preferably less than 15 minutes, more preferably less than 5 minutes, especially preferably less than 2 minutes and most preferably less than 1 minute. In general, it is preferred to select the residence time of the evaporation stage such that a shorter residence time is established correspondingly at higher bottom temperatures.

As mentioned above, the evaporator with short residence time can be connected to more than one further evaporator with short residence time, for example to 2 or 3 evaporators, in which case the last of the evaporators in the chain constitutes the so-called last evaporation stage. The residence time and the temperatures in the last evaporation stage correspond to the residence times and temperatures of the second evaporation stage in the two-stage configuration.

In the preparation of NPG using TMA as the tertiary amine, in the first evaporation stage, a bottom temperature of 135 to 170° C., more preferably 150 to 160° C., can preferably be established at a residence time of less than 45 minutes, preferably less than 30 minutes. In the second evaporation stage, a temperature of 160 to 220° C., preferably 180 to 200° C., is preferably established at a residence time of less than 15 minutes, preferably less than 10 minutes and more preferably less than 5 minutes.

The distillation column preferably has internals for increasing the separating performance. The distillative internals may, for example, be present as a structured packing, for example as a sheet metal packing such as Mellapak 250 Y or Montz Pak, B1-250 type. It is also possible for a structured packing with relatively low or increased specific surface area to be present, or it is possible to use a fabric packing or a structured packing with another geometry such as Mellapak 252 Y. What are advantageous in the case of use of these distillative internals are the low pressure drop and the low specific liquid holdup compared to, for example, valve trays. The internals may be present in one or more sections.

The hydrogenation discharge is preferably fed in within a spatial region between ¼ and ¾ of the theoretical plates of the distillation column, more preferably within a spatial region between ⅓ and ⅔ of the theoretical plates of the distillation column. For example, the feed may be somewhat above the middle of the theoretical plates (ratio 3:4).

The number of theoretical plates is generally in the range from 5 to 30, preferably 10 to 20.

Under these conditions, in general, for the preferred polymethylols (neopentyl glycol, trimethylolpropane, trimethylolethane and trimethylolbutane), the lower-boiling polymethylol of the formula (I) is removed from the higher-boiling hydroxy acid of the formula (IV). When other polymethylols are used in the process, it may be necessary to select other pressure and temperature conditions, in order that the polymethylol can be removed from the hydroxy acid.

In the condenser, purified polymethylol is preferably obtained as the condensate.

The purity of the polymethylol is preferably at least 99.0% by weight, more preferably at least 99.2% by weight.

The composition obtained as the condensate preferably comprises, polymethylol of the formula (I) and 1 to 10 000 ppm by weight of the ester of polymethylol of the formula (I) and hydroxy acid of the formula (IV), preferably 5 to 5000 ppm by weight and more preferably 10 to 1000 ppm by weight of the ester of polymethylol of the formula (I) and hydroxy acid of the formula (IV).

The composition obtained as a condensate generally additionally comprises a small proportion of polymethylol formate.

The present invention accordingly also relates to a composition comprising polymethylol of the formula (I) and 1 to 10 000 ppm by weight of polymethylol formate, preferably 5 to 5000 ppm by weight and more preferably 10 to 1500 ppm by weight of polymethylol formate.

The uncondensed residual vapors comprise generally, as well as leakage air and traces of water, predominantly NPG, and are advantageously recycled directly in gaseous form into the distillation.

Preference is given to discharging, from the bottom of the evaporator, a discharge which comprises predominantly higher-boiling compounds, such as hydroxy acids of the formula (IV), for example hydroxypivalic acid (HPS).

The bottoms can either be utilized thermally in an incineration or be fed to a downstream distillation column, by fractionating it into several fractions.

For example, the bottoms from the NPG preparation can be fractionated into a low-boiling fraction, in particular containing HPA, a medium-boiling fraction, in particular containing HPN (>97% HPN), and a high-boiling fraction (in particular esters of HPA and HPN).

The advantages of the present invention are that the process according to the invention provides polymethylols with a small proportion of polymethylol formates. The polymethylols obtained by the process according to the invention are thus particularly suitable for use in polymers or networks, such as varnishes and coatings, in which bonds can be cleaved by acid-catalysis, for example in polyesters or polyurethanes. The polymethylols obtained by the process according to the invention have a high stability in these applications.

It is most preferably possible to use polymethylols with a content of polymethylol formate of less than 10 000 ppm by weight, preferably less than 5000 ppm by weight and more preferably less than 1500 ppm by weight to improve hydrolysis stability in polymers or networks. More particularly, it is also possible with preference to use a composition comprising polymethylol of the formula (I) and 1 to 10 000 ppm by weight of polymethylol formate, preferably 5 to 5000 ppm by weight and more preferably 10 to 1500 ppm by weight of polymethylol formate to improve hydrolysis stability in polymers or networks.

A further advantage of the process according to the invention is that the polymethylols can be prepared with a very high yield. This leads overall to an improvement in the economic viability of the polymethylol preparation process.

The inventive separation of the by-products and products obtained allows the economic viability of the process to be improved further, since most of the components can be utilized in material form, for example by recycling into the process. The proportion of compounds which have to be sent to disposal is reduced, such that the disposal costs in the process according to the invention can be reduced.

The invention is illustrated by the following examples:

Example 1

Preparation of an Aqueous Polymethylol Mixture by the Hydrogenation Process

Stage a) Aldol Reaction:

Approx. 750 g/h of isobutyraldehyde (approx. >99.5 GC area % of IBA) were reacted with approx. 700 g/h of formaldehyde (approx. 49% formaldehyde, 1.5% of methanol, remainder water) and 80 g/h of trimethylamine solution (50% TMA in water) in a two-stage stirred tank cascade.

Stage b) Distillative Separation of the Reaction Mixture from Stage a):

Subsequently, the solution was freed of low boilers by distillation in a column. The column was equipped with 1.5 m of fabric packing (specific surface area 500 m$^2$/m$^3$) in the rectifying section and 4 m of sheet metal packing (250 m$^2$/m$^3$). The aldolization discharge was fed in above the sheet metal packing. At the top of the column, a condenser with cooling water (approx. 10° C.) and a downstream phase separator was used. At the top, the distillate was fed to the condenser in gaseous form. Approx. 255 g/h of liquid condensate were obtained. In the phase separator connected downstream, an aqueous phase of 95 g/h was removed and fed completely to the column. In addition, 135 g/h were fed from the phase separator to the first stirred tank. In order to maintain the regulation temperature in the column at 85° C., 25 g/h of organic phase were additionally fed to the column. In the cold trap connected downstream of the condenser, approx. 1 g/h of liquid was obtained (approx. 80% IBA, approx. 20% TMA), which was likewise recycled.

The IBA removal was conducted at a top pressure of approx. 1 bar absolute. The evaporator used was a falling film evaporator. A bottom temperature in the bottom of the column of 104° C. was established. The reflux rate (i.e. cooling water rate of the partial condenser) to the column was regulated by means of the temperature in the middle of the fabric packing; a temperature of 85° C. was established.

By means of a pump, approx. 100 kg/h of liquid were drawn off from the bottom of the column. This was fed to the falling film evaporator (consisting of an oil-heated stainless steel tube, length 2.5 m, internal diameter approx. 21 mm, wall thickness approx. 2 mm). Approx. 1.5 kg/h of product with a concentration of approx. 0.3% isobutyraldehyde were drawn off from the bottom of the falling film evaporator. The vapors and excess liquid were fed to the bottom of the column. The bottom product discharged comprised approx. 70% by weight of HPA, approx. 1.5% by weight of HPN, 0.3% by weight of IBA, remainder water.

Stage c) Hydrogenation of the Bottom Discharge from Stage b):

The resulting bottom product was subsequently subjected to a hydrogenation by means of a fixed bed.

The catalyst was activated as follows:

150 ml of a Cu/Al$_2$O$_3$ catalyst as described in EP 44444 and PF57216 were activated in a tubular reactor at 190° C. by passing over a mixture of 5% by volume of hydrogen and 95% by volume of nitrogen (total volume 50 l (STP)/h) at ambient pressure for 24 hours.

The hydrogenation was performed as follows:

The starting solution used was the mixture described above as hydrogenation feed. Approx. 10% by weight based on the hydrogenation feed of a 15% aqueous solution of trimethylamine was added to the mixture. The feed thus obtained was conducted in trickle mode at H$_2$ pressure 40 bar through the reactor heated to 120° C. The space velocity was 0.4 kg of HPA/(I$_{cat}$*h). A portion of the hydrogenation discharge was added again to the feed (circulation mode). The ratio of circulation to feed was 10:1. The pH of samples of the reactor discharge at room temperature was measured at 8.9.

The composition of the aqueous polymethylol mixture from stage c) was:

NPG: 69% by weight
Methanol: 3.5% by weight
TMA: 2% by weight.
organic secondary compounds (HPA, isobutanol): <2% by weight
TMA formate: 1% by weight
Water: 23% by weight

Example 2

Distillation of an Aqueous Polymethylol Mixture from Stage c)

The discharge obtained from the hydroxypivalaldehyde hydrogenation was fed to a distillative separation. A packed column (DN 50 mm) with three sequences of structured packing each of length 1 m and specific surface area 500 m$^2$/m$^3$ was used. The feed is above the lowermost sequence. A top pressure of approx. 175 mbar absolute was established. In the bottom, a temperature of 164° C. was established. The value of 164° C. corresponds to 110% of the boiling point of NPG formate at 175 mbar.

The energy was supplied to the column by means of a natural circulation evaporator. The vapors obtained at the top were fed to a condenser; this precipitates the vapors obtained virtually completely at 30° C. The vacuum was obtained by means of a simple commercial waterjet vacuum pump. Approx. 350 g/h of the distillate obtained were discharged; approx. 250 g/h were metered into the column at the uppermost packing section as reflux. The water used to obtain the vacuum was sent to biological wastewater treatment.

Crude NPG with the following composition was obtained in the bottoms:

97% by weight of NPG with approx. 400 ppm by weight of NPG formate.

COMPARATIVE EXAMPLE

Under otherwise identical conditions to those in example 2, the boiling rate in the bottoms was reduced to 75 g/h by reduction of the reflux. A temperature of 145° C. was established in the bottoms. Crude NPG with the following composition was obtained in the bottoms:
97% by weight of NPG with approx. 5700 ppm by weight of NPG formate.

Example 3

Distillation of an Aqueous Polymethylol Mixture from Stage c)

The discharge obtained from the hydroxypivalaldehyde hydrogenation was fed to a distillative separation. A packed column (DN 50 mm) with three sequences of structured packing each of length 1 m and specific surface area 500 m²/m³ was used. The feed is above the lowermost sequence. A top pressure of approx. 70 mbar absolute was established. In the bottom, a temperature of 148° C. was established. The value of 148° C. corresponds to 120% of the boiling point of NPG formate at 70 mbar.

The energy was supplied to the column by means of a natural circulation evaporator. The vapors obtained at the top were fed to a condenser; this precipitates the vapors obtained virtually completely at 10° C. The vacuum was obtained by means of a simple commercial waterjet vacuum pump. Approx. 350 g/h of the distillate obtained were discharged; approx. 250 g/h were metered into the column at the uppermost packing section as reflux. The water used to obtain the vacuum was sent to biological wastewater treatment.

Crude NPG with the following composition was obtained in the bottoms:
97% by weight of NPG with approx. 400 ppm by weight of NPG formate.

Example 4

Distillation of an Aqueous Polymethylol Mixture from Stage c)

The discharge obtained from the hydroxypivalaldehyde hydrogenation was fed to a distillative separation. A packed column (DN 50 mm) with three sequences of structured packing each of length 1 m and specific surface area 500 m²/m³ was used. The feed is above the lowermost sequence. A top pressure of approx. 500 mbar absolute was established. In the bottom, a temperature of 189° C. was established. The value of 189° C. corresponds to 106% of the boiling point of NPG formate at 500 mbar.

The energy was supplied to the column by means of a natural circulation evaporator. The vapors obtained at the top were fed to a condenser; this precipitates the vapors obtained virtually completely at 50° C. The vacuum was obtained by means of a simple commercial waterjet vacuum pump. Approx. 350 g/h of the distillate obtained were discharged; approx. 250 g/h were metered into the column at the uppermost packing section as reflux. The water used to obtain the vacuum was sent to biological wastewater treatment.

Crude NPG with the following composition was obtained in the bottoms:
97% by weight of NPG with approx. 400 ppm by weight of NPG formate.

The invention claimed is:
1. A process for distilling an aqueous polymethylol mixture comprising a polymethylol of the formula (I)

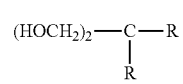

in which each R is independently a further methylol group or an alkyl group having 1 to 22 carbon atoms or an aryl or aralkyl group having 6 to 22 carbon atoms, a tertiary amine,
water and
the adduct of tertiary amine and formic acid (amine formate), wherein the aqueous polymethylol mixture is obtained in a multistage reaction involving, in stage a), condensing alkanals in an aldol reaction with formaldehyde in the presence of tertiary amines as a catalyst to give methylolalkanals of the formula (II) where each R is independently a further methylol group or an alkyl group having 1 to 22 carbon atoms or an aryl or aralkyl group having 6 to 22 carbon atoms

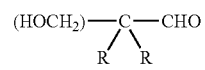

and then, in stage b), distillatively separating the reaction mixture obtained from stage a) into bottoms comprising predominantly compounds of the formula (II), and a top stream comprising low boilers, and, in stage c hydrogenating the bottoms discharge from stage b), wherein the reaction discharge from the hydrogenation (stage c)) is an aqueous polymethylol mixture which comprises a polymethylol of the formula (I) and the aqueous polymethylol mixture is purified by removing low boilers from the polymethylol compound by distillation, wherein the distillation is performed in a distillation column which is connected at the bottom to an evaporator, the temperature at the bottom of the column being above the evaporation temperature of the monoester of formic acid and polymethylol (polymethylol formate) which forms during the distillation and wherein the reflux at the top of the column is adjusted such that the predominant amount of the polymethylol formate is retained in the column, and discharged from the bottom of the evaporator is a discharge which comprises predominantly the polymethylol compound.

2. The process according to claim 1, wherein the aqueous polymethylol mixture comprises
20 to 90% by weight of polymethylol (I),
0 to 5% by weight of methanol,
0 to 5% by weight of tertiary amine,
0 to 5% by weight of organic secondary compounds,
0.01 to 5% by weight of the adduct of tertiary amine and formic acid (amine formate), and the remainder water.

3. The process according to claim 1, wherein the polymethylol is neopentyl glycol, trimethylolpropane, pentaerythritol, trimethylolethane, or trimethylolbutane.

4. The process according to claim 3, wherein the polymethylol is neopentyl glycol.

5. The process according to claim 1, wherein the tertiary amine is triethylamine, tri-n-propylamine, tri-n-butylamine, or trimethylamine.

6. The process according to claim 4, wherein the tertiary amine is trimethylamine.

7. The process according to claim 5, wherein the tertiary amine is trimethylamine.

8. The process according to claim 1, wherein the pressure at the top of the column is 0.001 to 0.9 bar, the column further comprises a condenser, and the operating temperature of the condenser is in the range from 0 to 80° C.

9. The process according to claim 1, wherein the temperature of the bottom of the column is 10% to 50% above the boiling temperature of the polymethylol formate.

10. The process according to claim 1, wherein the distillation column further comprises a condenser, and more than 30% by weight condensate obtained in the condenser is recycled into the distillation column.

11. The process according to claim 1, wherein the distillation column has 5 to 30 theoretical plates.

12. The process according to claim 1, wherein the distillation column has internals for increasing the separating performance and the aqueous polymethylol mixture is fed in within a spatial region between ¼ and ¾ of the theoretical plates of the distillation column.

13. The process according to claim 1, wherein tertiary amine is added to the bottoms discharge from stage b).

14. The process according to claim 1, wherein the bottoms discharge from the distillation of the aqueous polymethylol mixture is separated into a top stream comprising polymethylol, and a bottom stream comprising higher-boiling organic components.

* * * * *